United States Patent
Ringold

(10) Patent No.: US 9,334,525 B2
(45) Date of Patent: May 10, 2016

(54) METHOD AND APPARATUS FOR DETECTING CANCER IN MAMMALS

(75) Inventor: Randy Ringold, West Hills, CA (US)

(73) Assignee: Veterinary Diagnostics Institute, Inc., Simi Valley, CA (US)

( * ) Notice: Subject to any disclaimer, the term of this patent is extended or adjusted under 35 U.S.C. 154(b) by 0 days.

(21) Appl. No.: 14/372,328

(22) PCT Filed: Jan. 30, 2012

(86) PCT No.: PCT/US2012/023135
§ 371 (c)(1),
(2), (4) Date: Jul. 15, 2014

(87) PCT Pub. No.: WO2013/115772
PCT Pub. Date: Aug. 8, 2013

(65) Prior Publication Data
US 2014/0335552 A1    Nov. 13, 2014

(51) Int. Cl.
*C12Q 1/48* (2006.01)
*G01N 33/574* (2006.01)

(52) U.S. Cl.
CPC .......... *C12Q 1/485* (2013.01); *G01N 33/57488* (2013.01); *G01N 2333/9122* (2013.01); *G01N 2800/7028* (2013.01)

(58) Field of Classification Search
CPC .............................................. G01N 2333/9122
See application file for complete search history.

(56) References Cited

PUBLICATIONS

Kaaks et al. J of the National Cancer Institute, 2000, 92(19):1592-1600.*
Polanski et al. Biomarker Insights, 2006, 2:1-48.*
Lundqvist et al. Eur. J. Gynaec. Oncol., 1989, 10(6):395-405.*

* cited by examiner

*Primary Examiner* — Bin Shen
(74) *Attorney, Agent, or Firm* — Karim Lagobi

(57) ABSTRACT

The invention provides a method and apparatus for detecting cancer using the measurement of acute-phase proteins (APPs) and the measurement of thymidine kinase activity level in body fluids. An index is calculated based on the measured data and compared with a pre-established reference that allows a practitioner to determine a high probability that a patient is a carrier of cancer.

2 Claims, 4 Drawing Sheets

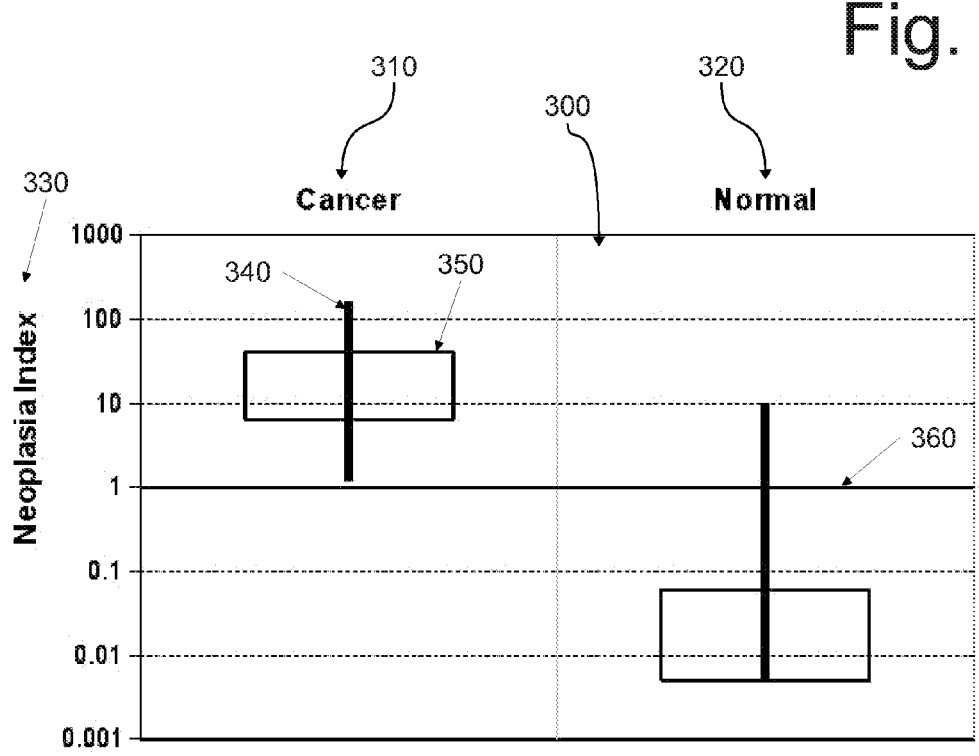

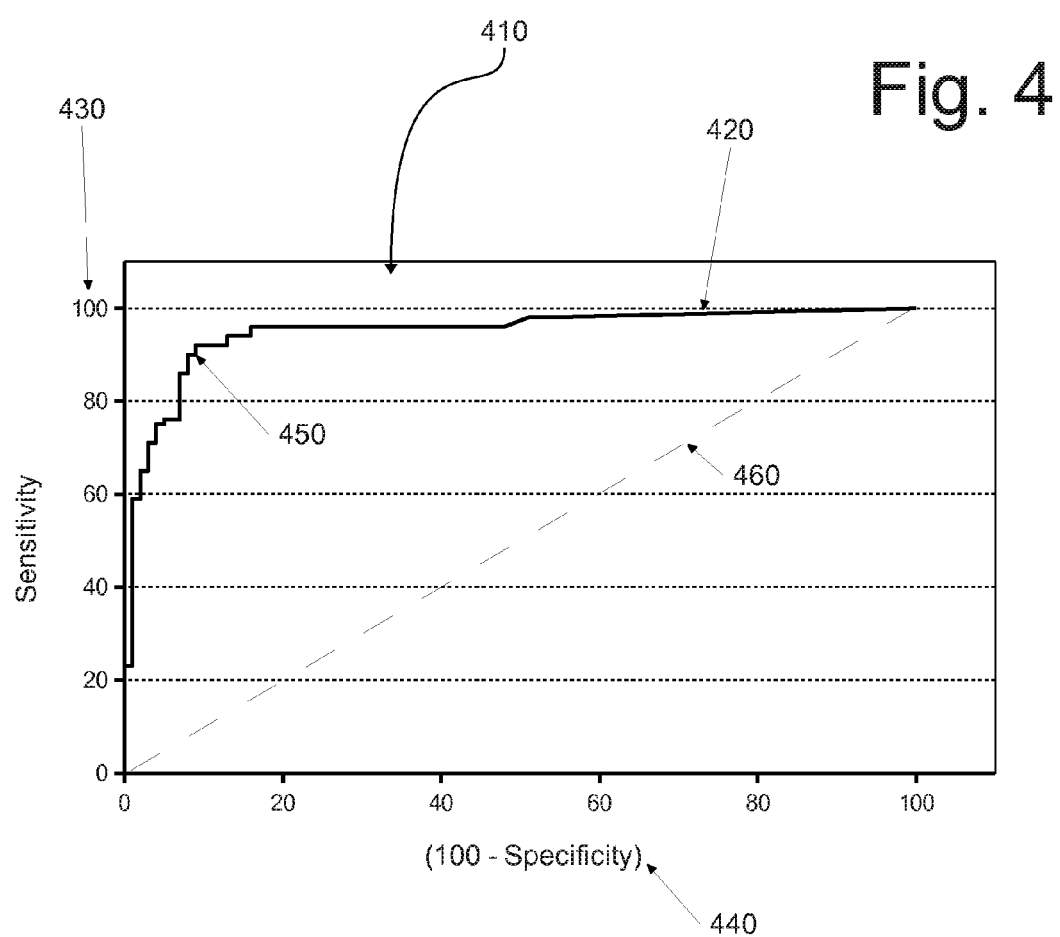

METHOD AND APPARATUS FOR DETECTING CANCER IN MAMMALS

CROSS-REFERENCE TO RELATED APPLICATION

This application is a national phase US application claiming priority to PCT application number PCT/US12/23135 filed on Jan. 30, 2012, the content of which is included herein in its entirety by reference.

FIELD OF THE INVENTION

The invention relates to a method and apparatus for detecting cancer. More specifically, the invention comprises a method and apparatus for providing an index pointing to the presence of cancer in a mammalian subject using the measurement of one or more biomarkers.

BACKGROUND OF THE INVENTION

The incidence of cancer in both humans and animals is increasing. Due to an ever increasing life expectancy and environmental factors, the incidence of cancer-related medical claims is increasing year after year. Among the known cancer-causing/contributing factors are microbial infections (e.g., virii), chemicals and radiation exposure and genetic inheritance. These factors can cause numerous types of cancers, the virulence of which depends on the affected tissue/organ, the location in the body and the reaction of the body to the cancer.

Treatment for cancer is improving with an ever growing range of available drugs and radiation treatments even though the diagnosis of the cancer type and location and subsequently the treatment and the monitoring have to be carefully devised on a patient-by-patient basis, given the large number of different types of cancer. However, one common aspect that significantly improves the success rate of treatment is early detection. For most cancer types early detection improves the outcome of the treatment and the management of the disease.

Since early detection of cancer plays such a crucial role in the success of the treatment (e.g., survival rate of patients), the screening of some cancers (e.g., breast cancer, colon cancer) may be recommended even in subjects appearing healthy and without showing symptoms that may be attributed to cancer. However, screening is typically a medical (or veterinary) procedure that may be invasive (e.g., requires biopsies) and is generally too expensive to make it a routine procedure in non-suspected patients. Additionally, because of the cost a practitioner may be reluctant to order a full screening for cancer when a patient is showing only mild symptoms or a few symptoms that would indicate cancer.

Therefore, there is a need for screening methods for cancer that are cost effective, and least invasive allowing a practitioner to detect cancer at an early stage and pursue other methods of diagnosis and treatment. The same methods may be used to monitor subjects during and after treatment cost-effectively.

SUMMARY OF THE INVENTION

The invention allows a practitioner to screen for cancer and develop screening tools using body fluids such as blood serum. The screening may be carried out cost-effectively in humans/animals with no overt symptoms/signs. Thus, enabling an early detection of cancer, which plays a crucial role in the success rate of subsequent treatment.

In patients that have been treated for cancer, implementations of the invention enable the practitioner to monitor the recovery of the patient and detect remissions.

The invention uses a combination of two or more biomarkers to detect the presence of cancer or the proliferation rate of cancer activity. One biomarker may be thymidine kinase and the others may be any number of acute-phase proteins (APPs). Acute-phase proteins may increase or decrease during inflammation, for example, due to cancer. In practice, the invention is implemented as a set of biochemical tests to measure the concentration of one or more APPs along with the measurement of the activity level of thymidine kinase, and compute an index that allows a practitioner to rule in (or out) the presence of cancer during a diagnostic.

BRIEF DESCRIPTION OF THE DRAWINGS

FIG. 3 shows a plot illustrating the segregation between two groups of dogs, one group affected by cancer and the second group is normal, using the neoplasia index in accordance with the teachings of the invention.

FIG. 4 is a plot showing the relationship between the sensitivity and the specificity of the neoplasia index, in accordance with an embodiment of the invention.

DETAILED DESCRIPTION OF THE INVENTION

Figure 1:
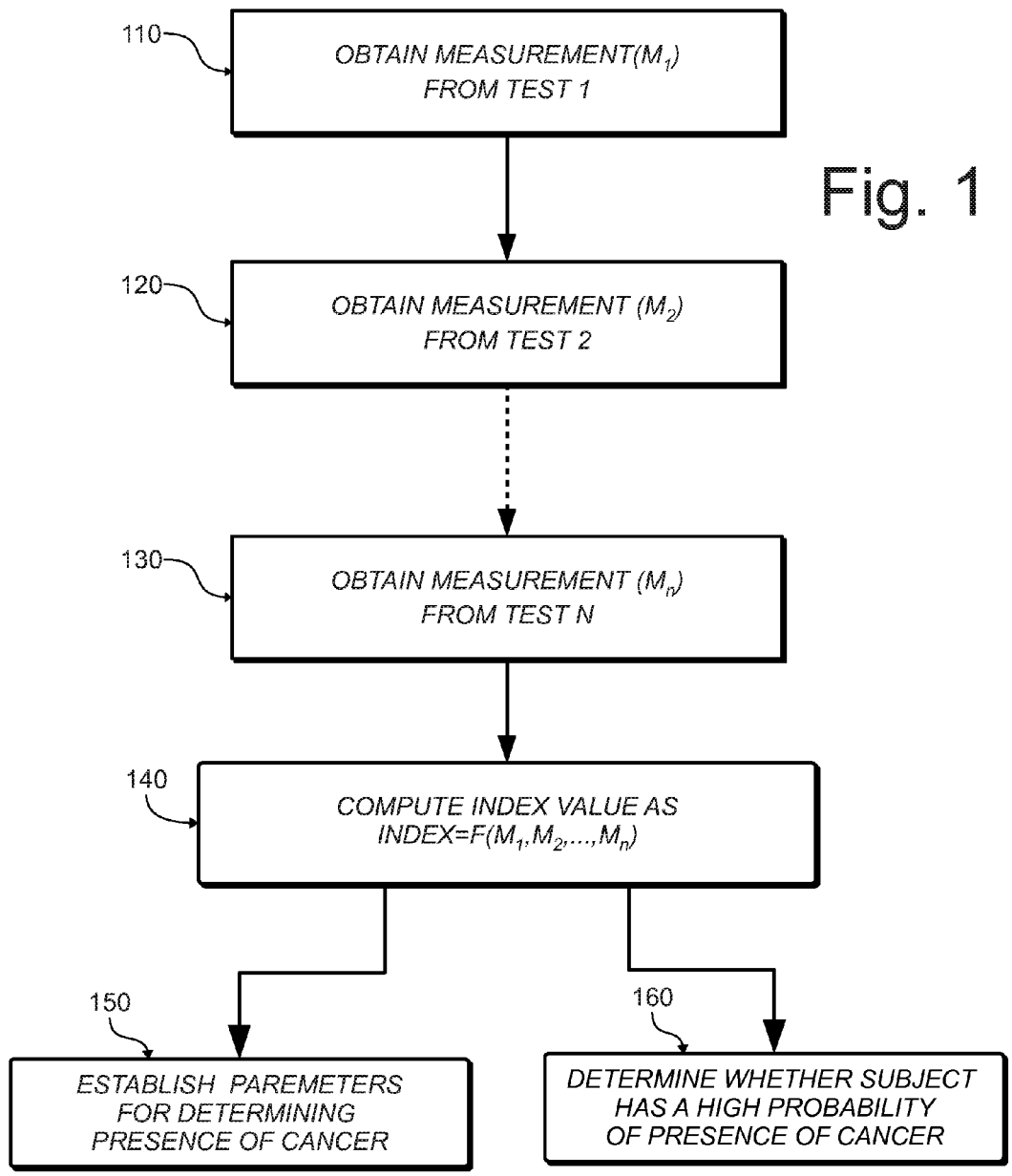
FIG. 1 is a schematic representation of steps involved in detecting cancer in accordance with an embodiment of the invention.

The invention teaches a method and apparatus by which a practitioner determines whether a human or another mammalian may be the carrier of a cancerous growth by measuring the presence of one or more biomarkers and computing an index that provides the likelihood of the presence of the cancerous growth.

In the following description, numerous specific details are set forth to provide a more thorough description of the invention. It will be apparent, however, to one skilled in the pertinent art, that the invention may be practiced without these specific details. In other instances, well known features have not been described in detail so as not to obscure the invention. The claims following this description are what define the metes and bounds of the invention.

The disclosure uses the term "biomarker" to refer to any biochemical substance, such as a protein, a peptide, ribonucleic acid (RNA), deoxyribonucleic acid (DNA) or any other molecule the concentration (or activity level) of which implementations of the invention may use as an indicator for the presence of cancer.

In the disclosure the measurement of biomarkers are typically concerned with measuring the concentration (or the activity level) of the biomarker in the blood serum. One with ordinary skills in the pertinent art would recognize that the invention may be practiced using other body fluids such as cerebrospinal fluid, lymph or any other body fluid for which the invention has been implemented. In addition, implementations of the invention may adequately select more than one body fluid for testing for each or any number of biomarkers considered in a test of detecting cancer.

In using an enzyme as a biomarker, the level of activity of the enzyme may depend on the type of substrate in the test kit, in addition to other parameters such as temperature and pH. Thus, the disclosure considers any adjustments to the calculation/measurement of the enzymatic activity a practitioner may make to practice the invention as inherent steps required for specific implementations of the invention without deviating from the concept of the invention.

The invention aims at providing cost-effective easy to implement screening for cancer. Therefore, an implementation for screening for cancer in accordance with the invention requires basic laboratory equipment for measuring proteins and/or enzymatic activity levels in body fluids, comprising body fluid collection kits (e.g., red top tubes, needles and syringes), body fluid storage and handling equipment, blood serum separation tools (e.g., centrifuges), test tubes and any other machine or tools for a laboratory test. The invention may be practiced using any available test kits for measuring any target biomarker for a specific implementation.

Cancers are malignant neoplasms (growth) that occur when cell division braking mechanisms malfunction. The cell division braking mechanisms consists of an ensemble of genes that function in concert to regulate cell division and differentiation and in many tissues prevent further cell division after differentiation. The causes of these genes malfunctions may be genetically inherited or caused by any of the numerous environmental factors. An individual's race (or breed) may particularly predispose the subject to cancer. In dogs, for example, Golden Retrievers and German Shepherds have a higher incidence of cancer than other breeds, with over 50% dying of cancer after the age of 10 years.

There has been a long standing and studied relationship between cancer and inflammation. The inflammatory response orchestrates the defenses in a body following an infection, trauma, toxins, or other tissue damaging events, and mediates tissue repair and regeneration. Epidemiological evidence points to a connection between inflammation and a predisposition for the development of cancer, i.e. long-term inflammation leads to the development of dysplasia. Epidemiologic studies estimate that nearly fifteen percent (15%) of the worldwide cancer incidence is associated with microbial infection. Chronic infection in immunocompetent hosts such as human papilloma virus or hepatitis B and C virus infection leads to cervical and hepatocellular carcinoma, respectively. In other cases, microbes may cause cancer due to opportunistic infection such as in Kaposi's sarcoma (a result of human herpes virus (HHV)-8 infection) or inappropriate immune responses to microbes in certain individuals, which may occur in gastric cancer secondary to *Helicobacter pylori* colonization or colon cancer because of long-standing inflammatory bowel disease precipitated by the intestinal microflora.

In many other cases, conditions associated with chronic irritation and subsequent inflammation predispose to cancer. For example, long-term exposure to cigarette smoke, asbestos, and silica are all factors that have been shown to lead to an increase of the incidence of cancer.

In cancer, there is evidence that inflammation plays an essential role at each stage of the disease (initiation and proliferation), and both tumor and inflammatory cells are able to directly or indirectly either inhibit or stimulate tumor growth. The effectiveness of tumor development has been demonstrated to correlate directly with the degree of the inflammatory reactions, and it seems that there are interactions between the cytokines produced in response to inflammatory reactions and tumor growth and even indications that inflammatory cytokines favor tumor promotion.

An inflammatory process leads to the activation of the cytokine network. In the early phase of this process, proinflammatory cytokines (TNF-α, IL-1β, INF-γ and IL-12) are released. The activity of proinflammatory cytokines is counteracted by the production of anti-inflammatory cytokines (IL-4, IL-10, IL-13 and TGF-β) and soluble inhibitors of proinflammatory cytokines (soluble TNF-α receptor, soluble IL-1 receptor, and IL-1 receptor antagonist).

In response to the formation of cytokines, a complex series of reactions are initiated called the acute-phase response (APR). These reactions aim to prevent ongoing tissue damage, isolate and destroy the infectious organism (if present) and activate the repair processes necessary to restore the host/organism's normal function. The acute-phase response is characterized by leukocytosis, fever, alterations in the metabolism of many organs as well as changes of the concentration of various acute-phase proteins (APPs) in the blood plasma.

Acute-phase proteins (APPs) have been defined as any protein the concentration of which in the plasma changes by at least twenty five percent (25%) during an inflammatory disorder. Those proteins the concentration of which increases are defined as positive acute-phase proteins (e.g., fibrinogen, serum amyloid A, albumin, C-reactive protein), and those proteins the concentration of which decreases are defined as negative acute-phase proteins (e.g., albumin, transferrin, insulin growth factor I).

For example, C-reactive protein (CRP) is a major APP and has been shown to be an effective measure of general inflammation. The concentration of CRP or any serum APP level correlates to both the severity and the duration of the inflammatory stimuli.

The invention utilizes any of the acute-phase proteins as a bio-marker. The increase or the decrease in the concentration of any number of APPs may be used to establish that an inflammation is associated (or caused by) the presence of a cancerous growth. Furthermore, the invention may utilize any number of biomarkers that are indicative of cell division, such as Thymidine kinase.

Thymidine kinase type 1 (TK) is a salvage enzyme involved in the synthesis of DNA precursors. Thymidine kinase is expressed only in phase S though G2 of cell division (Mitosis). TK levels have been shown in numerous studies, both in humans and animals, to correlate with the proliferative activity of tumor disease. Serum TK concentrations have been studied in human and veterinary applications. While originally thought to be an indicator only for hematopoietic cancers such as lymphoma and leukemia, TK has been recently studied in its application for screening in human subjects for the identification of head and neck tumors and in veterinary applications for hemangiosarcoma (R. Ringold et al., U.S. Pat. No. 8,097,432).

There are instances whereby TK may be elevated in non-neoplastic situations, and they have been shown to be transient elevations due to viral or other common cellular replication events and can lead to false positive results.

Embodiments of the invention may utilize the measure of TK activity in combination with measuring the concentration of one or more APPs, in order to evaluate the probability that a mammal is a carrier of cancerous growth.

FIG. 1 is a schematic representation of steps involved in detecting cancer in accordance with an embodiment of the invention. The steps in FIG. 1 may be practiced in both developing the methodology to determine the ranges of the indices for determining the probability of the presence of cancer, or testing an individual subject for comparison with a pre-established set of criteria.

At step 110, a blood test is carried out to measure the concentration (or the activity level) of a first biomarker. A biomarker is defined as any substance in the blood, or any other body fluid, the concentration of which may be affected by the presence of cancer in the body. For instance, the measurement ($M_1$) in step 110 may be concerned with measuring the activity level of TK., a protein or any other substance selected for its association with the presence of cancer. The invention also teaches any one of the target biomarkers may be measured in the blood serum, cerebrospinal fluid, lymph or any other body fluid that may carry the target biomarker.

At step 120, an embodiment of the invention measures the concentration (or the activity level) of a second biomarker known to be associated with the presence of cancer in a mammal. The process in steps 110 and/or 120 may be repeated for a number of biomarkers as represented by step 130, in order to the determine the concentration (and/or activity levels) or any number of bio-markers. Steps 110, 120 and 130 may be carried out using any available method, and test kits available to measure the concentration (and/or activity level) of the biomarkers chosen for a given test in accordance with embodiment of the invention.

Furthermore, the measurement steps may be conducted simultaneously, sequentially and/or repeated (for statistical accuracy) by the same practitioner or by separate practitioners in the same (or in separate) facilities.

The methodology embodiments of the invention may utilize antibodies that are specific to each APP (e.g., CRP). An antibody (e.g., anti-CRP antibody) binds specifically to a target protein. Most measurement kits are devised such that the antibody is revealed though a molecule that binds itself to the antibody and that is conjugated with a photo-marker. The photo-marker is typically designed to absorb light at one or more specific wave lengths. Thus by measuring the absorption of light, one is able to determine the concentration of the target protein, by reading/calculating the concentration using a chart of absorption versus concentration.

At step 140, the data is collected from the measurements conducted in steps 110 through 130, and an algorithm is applied to the data to produce an index value. The general algorithm is represented as follows (see Formula 1):

$$I = F(M_1, M_2, \ldots, M_n) \quad (1)$$

Where "I" is the calculated index that allows a practitioner to make a determination of the presence of cancer, "F" is the function that embodies the calculation using the measured result and pre-established data (normal data obtained from cancer-free subjects) and other parameters that may be introduced to further improve the accuracy (or the information content of the results).

For example, in embodiments of the invention the index function may be a multiplication of the concentration and/or activity measure of two or more biomarkers. The general formula to compute index "I" may be as follow:

$$I = K \cdot \pi C_n^{W_n} \quad (2)$$

Where "$C_n$" is the measured concentration "C" of the "$n$"$^{th}$ biomarker from a patient, "K" is a normalization factor, and "$W_n$" is weighting exponent associated with the $n^{th}$ biomarker. "C" may be calculated as a deviation of a measured quantity "$C_m$" versus a pre-established "normal" quantity "$C_0$" as follows:

$$C = C_m - C_0 \quad (3)$$

In instances where an embodiment of the invention uses a negative acute-phase protein, the absolute or the squared value of the difference between the measured concentration "$C_m$" and a reference (normal) concentration "$C_0$" may be considered.

The weighting exponent may be selected to attribute a higher (or alternatively lesser) degree of importance to the informative content of a deviation of a biomarker from its normal value (or range thereof). The weighting exponent may be adjusted on the basis of several factors, such as the patient's species, age, gender and any other parameter that may affect the relevance of the increase (or decrease) of a biomarker in determining the presence of cancer. The weighting exponent may also be established based on a pre-determined threshold above (or below) which the presence of a biomarker may become relevant in the index calculation. The weighting exponent may take into account the standard deviation in a cancer-free population in order to determine the relevance level of measured values of a given biomarker in a patient with regard to other measured biomarkers in the same patient.

As shown in Formula 2, the invention teaches that the product of all the measured values may be compared with a threshold (cutoff) value. When the "measured" product is above (or below as a case may require) the set threshold, the test may be considered positive i.e., the subject may have a high probability of having cancer. Using the cutoff value, the normalization factor "K" may be selected as 1/cutoff value. For example, a calculated index value above "1" may indicate that a subject is likely carrier of a cancer i.e., the product of the measured values is above the cutoff value.

In other embodiments, the computation may involve summing the values of all measured biomarkers, as follows:

$$I = \sum_{n=1}^{n=N} W_n \cdot C_n \quad (4)$$

where "C" may take the values as in Formula (2). "$W_n$" may be a weighting coefficient associated with the $n^{th}$ biomarker. The weighting coefficient in Formula 4 plays a similar role as the weighting exponent in Formula 2.

Step 150 represents the process through which experimental and/or clinical data may be analysed in order to determine a cutoff value using one or more biomarkers. For example, the result of sampled subjects from a healthy population maybe compared to a population with proven existence of a given cancer. The data may be analysed using the Receiver Operating Characteristic (ROC) curves, which allows a user to establish a cutoff value for a given biomarker between populations of healthy and affected subjects. A meaningful biomarker is one for which the cutoff value yields the highest sensitivity and the highest specificity of the test. In addition, the invention teaches using a compounded cutoff value from two or more biomarkers. Using the calculation of an index (e.g., using formula 1 or 2), an embodiment of the invention allows for determining a compounded cutoff value for any number of biomarkers.

Step 160 represents the process by which the data from a subject is used to calculate an index and compare the calculated value to a reference value (or a range thereof), to determine whether the patient is likely a carrier of cancer and further diagnostic methods for cancer should be recommended. Step 160 may further be carried out post-treatment in order to monitor progress and/or reveal remissions.

Figure 2:
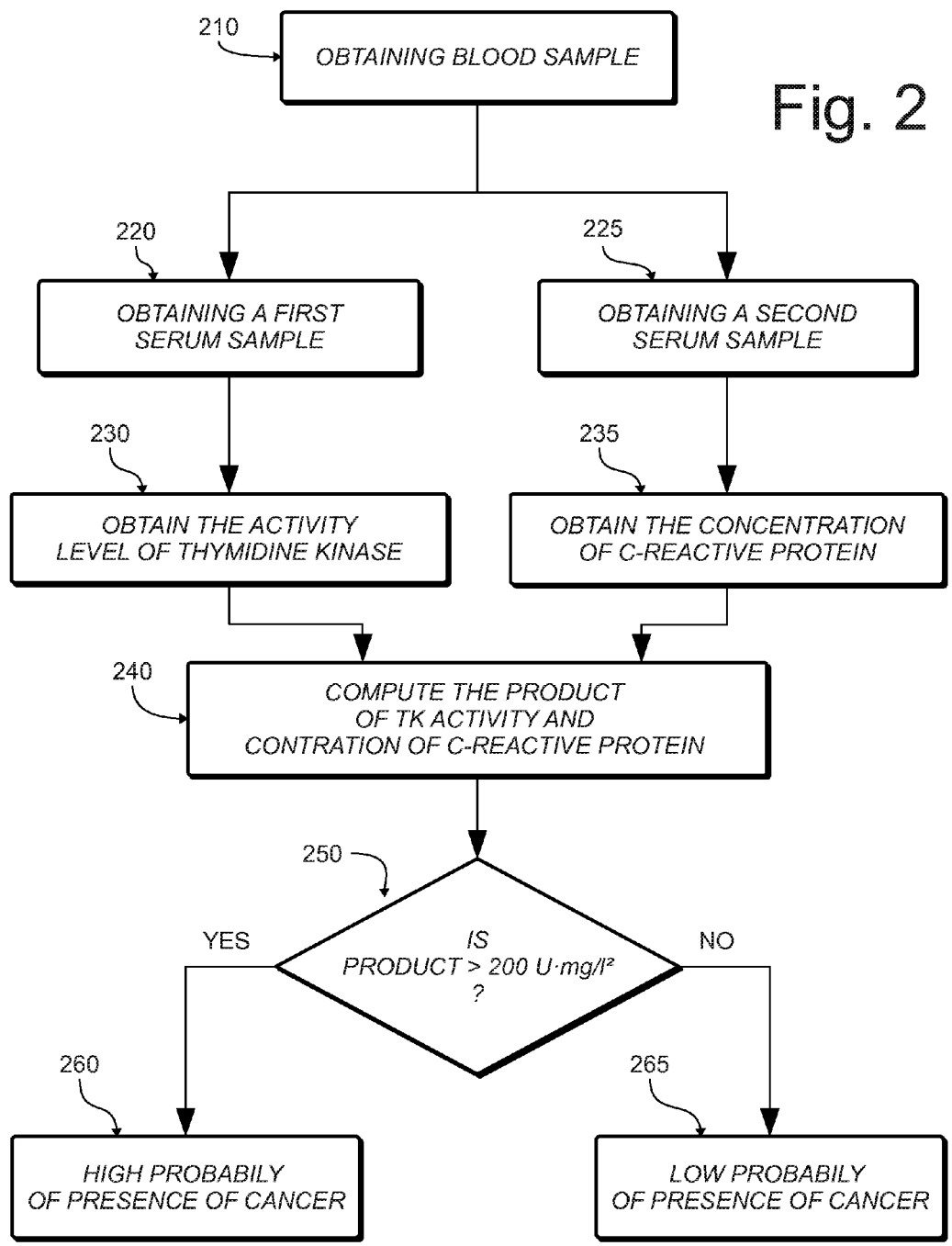
FIG. 2 schematically represents steps involved in assessing the presence of cancer using thymidine kinase activity level and the concentration of c-reactive protein to assess the presence of cancer in accordance with an embodiment of the invention.

The invention teaches a method by which measurement of the activity level of TK is combined with the concentration of c-reactive protein present in the blood serum to compute an index for assessing the presence of cancer. FIG. 2 schematically represents steps involved in assessing the presence of cancer using thymidine kinase activity level and the concentration of c-reactive protein to assess the presence of cancer in accordance with an embodiment of the invention. TK activity and CRP concentration are combined into a "neoplasia index", which brings two unrelated processes together (namely abnormal cell division and a measure of general inflammation for which cancer may be one possible cause) and effectively amplifies the situation whereby the two indicators may be elevated in-concert, thus indicating the presence of cancer. This amplification drastically improves the performance for cancer detection in subjects appearing to be healthy in both human and veterinary applications.

Like the process described in FIG. 1, the steps in FIG. 2 may be practiced in both developing the methodology to determine the ranges of the indices for determining the probability of the presence of cancer, or testing an individual subject for comparison with a pre-established range for the indices.

At step 210, blood (and/or any other body fluid required for testing) is collected from a subject. At step 220 and step 225, a serum portion of the blood is obtained for each target testing. For example, a first sample may be obtained for testing TK activity whereas a second sample may be obtained for measuring the concentration of CRP. The collected blood portion may be submitted to centrifugal force (using a centrifuge) to separate the serum portion from the blood cells portion. Embodiments of the invention may use any available methodology to measure TK activity and CRP. Thus, if the available methodology does not require a separation of a serum portion from the blood, then the implementation of the invention may forego step 220 and/or 225 depending on the requirement for the measurement kit in use.

At step 230, the level of TK activity is measured. The measurement of TK activity level may utilize any available methodology and/or available TK measuring kit. For example, TK activity level may be measured using an assessment kit provided by DiaSorin®, the use of the kit is described in detail in U.S. Pat. No. 8,097,432, which is included herein in its entirety by reference. In addition, an implementation of the invention may be practiced with an indirect means for measuring the activity of TK using, for example, substrates other than thymidine and Adenosine triphosphate (ATP) as a phosphate donor. In the latter case, the measured data may be converted to reflect the real concentration (in mass/volume units) of the enzyme in order to obtain data that is comparable with pre-determined data values (normal value).

At step 235, the concentration of c-reactive protein (CRP) is measured. The measurement of CRP concentration may be carried out with any available protein measuring methodology for specifically determining the concentration of CRP in the blood. For example, in canine application, a practitioner may utilize the canine CRP ELISA kit by the TECO® Medical Group.

At step 240, an index i.e. neoplasia index is calculated using the TK activity level and the concentration of CRP. Because an index was developed on the basis of conveying information about the presence of cancer, the algorithm for calculating the index may take into account the actual information value of each measurement in the assessment. For example, since the increase of TK activity in an organism is indicative of the presence of cancer, and since that information is further reinforced by an increase in the concentration of CRP, the values obtained from the latter two measurement may be multiplied. The general formula for computing the neoplasia index based on TK and CRP measurement may be based on the general formula (2), as follow (see formula 5):

$$I = K \cdot [TK] \cdot [CRP] \quad (5)$$

where "K" may be a normalization factor; "[TK]" is the concentration of TK present in the blood, which may be expressed in units of activity per volume (e.g., U/l); and "[CRP]" is the concentration of CRP as may expressed in mass per volume (e.g., mg/dl). The invention contemplates the use of weighting exponents as in formula 2 in order to further refine the information content of the test. One embodiment of the invention uses weighting exponents equal to 1 i.e. each biomarker has an equal amount to informative value.

A canine model to demonstrate this invention was conducted with a cohort of 337 patients. Statistical analysis results of the study as processed, using Receiver Operating Characteristic (ROC) curves, are presented in Table 1, FIG. 3 and FIG. 4.

TABLE 1

| | |
|---|---|
| Sample size: | 390 |
| Positive group: | 52 |
| Negative group: | 338 |
| Disease prevalence: | 13.2% |
| Area Under ROC Curve: | 0.953 |
| Standard Error: | 0.0181 |
| 95% Confidence Interval: | 0.927 to 0.972 |
| z statistics: | 25.081 |
| Significance Level P (Area = 0.5): | <0.0001 |

The study determined that a subject showing a product value of TK and CRP above 20 U/l·mg/dl (or 200 U·mg·l$^{-2}$) has a high probability of carrying cancer. The normalization factor "K" may be selected as having value "1/cutoff" (e.g., 1/20 U/l·mg/dl). Thus, according to Formula 5, a practitioner may refer to value "1" as being the threshold value above which a canine subject should be referred for further testing for cancer.

FIG. 3 shows a plot illustrating the segregation between two groups of dogs, one group affected by cancer and the second group is normal, using the neoplasia index in accordance with the teachings of the invention. Plot 300 shows the data plots for a group affect by cancer 310, and a "Normal" group 320 i.e. unaffected by cancer. The ordinate axis 330 shows the neoplasia index as computed according to Formula 5. The vertical bars (e.g., 340) represent the spread between the maximum and the minimum values of measured activities for each group. For each group, a box (e.g., box 350) represents the neoplasia index values, respectively, corresponding to the first quartile of the group, represented by the bottom of the box, and the third quartile of the group represented by the top of the box. The width of each box represents no statistical data. Line 360 graphically represents the threshold value "1" determined to be an indicator above which a subject may be categorized as having cancer.

FIG. 4 is a plot showing the relationship between the sensitivity and the specificity of the neoplasia index, in accordance with an embodiment of the invention. Plot 410 shows a curve 420 that plots the sensitivity of the neoplasia index as a function of the specificity for range of cutoff values. The sensitivity scale 430 is expressed between "0" and "100", "0" meaning that the chosen cutoff value provides a test that is not sensitive i.e. no subject is determined as having cancer, and "100" meaning that the test positively determines all subjects with cancer. The specificity values 440 are expressed in 100 minus the measured specificity.

In FIG. 4, curve 460 (straight line) represents the relationship between the specificity and the sensitivity, in a Receiver Operating Characteristic (ROC) analysis of an inconclusive hypothetical test. FIG. 4 shows that the invention provides a test for which the specificity and sensitivity relationship represented by curve 420 rises toward the 100% sensitivity level and remains above curve 460. Thus, the invention determines, that a chosen cutoff value (data point 450) of 20 U/I·mg/dl represents a specificity and sensitivity near 100% and 90%, respectively. The latter allows a practitioner to determine with accuracy whether a subject has cancer.

Thus, a method and apparatus for screening for cancer using the measuring of thymidine kinase activity in a body fluid combined with the concentration of one or more acute-phase proteins. The invention provides an index that allows a practitioner to determine a probability that a patient is likely a carrier of cancer.

What is claimed is:

1. A method for detecting cancer in dogs comprising:
    obtaining a sample of blood serum from a dog;
    obtaining a concentration of C-reactive protein in said sample;
    obtaining a thymidine kinase activity level in said sample;
    obtaining a product value by multiplying said concentration of C-reactive protein by said thymidine kinase activity level; and
    detecting within a specificity and a sensitivity near 100% and 90%, respectively, of a Receiver Operating Characteristic (ROC) analysis that said dog is likely a carrier of cancer if said product value is greater than a threshold value of about 200 Unit-milligram per squared liter.

2. The method of claim 1 wherein said step of obtaining said product value further comprising obtaining a cancer indicating index by dividing said product value by said threshold value, wherein said cancer indicating index further indicating the presence of cancer if said index is greater than about a value of one.

* * * * *